(12) United States Patent  
Browning

(10) Patent No.: US 8,556,507 B1  
(45) Date of Patent: Oct. 15, 2013

(54) METHOD AND APPARATUS OF FACILITATING X-RAYS

(76) Inventor: Bruce K Browning, Reseda, CA (US)

( * ) Notice: Subject to any disclaimer, the term of this patent is extended or adjusted under 35 U.S.C. 154(b) by 160 days.

(21) Appl. No.: 12/313,045

(22) Filed: Nov. 17, 2008

Related U.S. Application Data

(63) Continuation of application No. 11/233,262, filed on Sep. 22, 2005, now abandoned.

(60) Provisional application No. 60/616,268, filed on Oct. 6, 2004.

(51) Int. Cl.  
*H05G 1/00* (2006.01)

(52) U.S. Cl.  
USPC ............................................. 378/204; 378/62

(58) Field of Classification Search  
USPC .................................................... 378/62, 204  
See application file for complete search history.

(56) References Cited

U.S. PATENT DOCUMENTS

| 4,726,357 | A | * | 2/1988 | DeStefano | 601/41 |
| 5,242,348 | A | * | 9/1993 | Bates | 482/105 |
| 6,168,539 | B1 | * | 1/2001 | Maina | 473/424 |
| 6,264,574 | B1 | * | 7/2001 | Nelson et al. | 473/603 |
| 2007/0179021 | A1 | * | 8/2007 | Wang | 482/49 |

* cited by examiner

*Primary Examiner* — Hoon Song  
(74) *Attorney, Agent, or Firm* — Colin P. Abrahams

(57) ABSTRACT

A holder for use in x-rays comprises a shaped object to be held by a person while undergoing an x-ray, the shaped object having an outer surface defining an enclosed space and filler matter in the enclosed space. At least a portion of the outer surface and filler matter is comprised of a radiolucent material. The invention is also for a method of taking x-rays of a human by placing a shaped object in the hands of the human receiving the x-ray, and then directing the human to hold the shaped object in a specified manner such that the position of the human when holding the object in the specified manner causes internal body components of the human to be located relative to each other in a preferred manner for the x-ray.

14 Claims, 3 Drawing Sheets

METHOD AND APPARATUS OF FACILITATING X-RAYS

CROSS REFERENCE TO RELATED APPLICATIONS

This application is a continuation application of U.S. patent application Ser. No. 11/233,262 filed Sep. 22, 2005, which claims the benefit of U.S. Provisional Patent Application No. 60/616,268 filed Oct. 6, 2004, and both of which are incorporated herein by reference in its entirety.

FIELD AND BACKGROUND OF THE INVENTION

This invention relates to a method and devices for facilitating x-rays, and the images produced as a result thereof. Particularly, the invention is directed towards methods and apparatus for assisting people undergoing x-rays in positioning the body in an optimal or near optimal condition so that the x-ray images produced in an x-ray can be clearer, have better definition, be more accurate with respect to location of the body being x-rayed, and/or producing x-rays pictures which can be more easily be read.

X-rays of humans are a well known medical procedure and have been carried out, and continue to be carried out, as a standard diagnostic tool used by health practitioners. In general, an x-ray is a penetrating form of electromagnetic radiation, usually generated by accelerating electrons to high velocity, and suddenly stopping them by collision with a solid body. In the medical field, x-rays may typically be used to obtain images of internal body components.

In many instances, an x-ray will require the person or patient to be positioned in certain postures and manners, and to hold his/her arms, legs or other body parts in certain positions, in order to permit the x-ray machine to obtain a clear and readable image of a desired body part or parts. This is particularly the case where, for example, one body part such as the scapula, or shoulder blade, may overlap, cover or shield (in an x-ray context) another body part, such as the lungs. In such a situation, it is necessary for the proper taking of the x-ray to position the patient in an optimal manner so as to avoid, to the extent possible, the shielding or overlap of another body part in the x-ray picture, which would interfere with a proper diagnosis and/or reading of the image.

SUMMARY OF THE INVENTION

According to one aspect of the invention, there is provided a holder for use in x-rays, the holder comprising a shaped object to be held by a person while undergoing an x-ray, the shaped object having an outer surface defining an enclosed space and filler matter in the enclosed space, at least a portion of the outer surface and filler matter being comprised of a radiolucent material and/or a solid radiolucent material. The shaped object may have a shape selected from: spherical, round, square, rectangular, triangular, polygonal, geodesic.

Preferably, the shaped object is substantially ball shaped and comprises at least one handle on the outer surface thereof. Preferably, two handles are on substantially opposing sides of the ball shaped object, the handles comprising outwardly extending grip members having ends which are secured to the outer surface of the ball shaped object.

In one form, the handle comprises a flat elongate strip having opposing ends, and fastening means for securing the flat elongate strip to the outer surface near the opposing ends thereof. The handle may be adjustable in size. In another form, the handle comprises a first band and a second band of fabric secured to the outer surface of the shaped object at a selected distance from each other, the first and second bands each having an outer surface at least a portion of which has a Velcro™ textured configuration; and a grip member extending at least between the first and second bands, the grip member having a surface at least a portion of which has a Velcro™ textured configuration so that the grip member can be releasably attached to and removed from first and second bands in various arrangements.

Both the outer surface of the shaped object and the filler matter are preferably comprised entirely of radiolucent material. The filler matter may be comprised of a lightweight material, high density foam, or polyurethane foam.

In a preferred embodiment, the shaped object is a ball of diameter between 30 and 45 inches.

According to another aspect of the invention, there is provided a method of obtaining better quality x-rays of a human, the method comprising: forming a shaped object having an outer surface and a fill material which are both at least partially comprised of a radiolucent material; placing the shaped object in the hands of the human receiving the x-ray; and directing the human to hold the shaped object in a specified manner such that the position of the human when holding the object in the specified manner causes internal body components of the human to be located relative to each other in a preferred manner for the x-ray.

In one embodiment, the human is directed to hold the object by hugging the ball on or against the chest with the chin of the person resting on the ball. Such a position is suitable obtaining an anterior-posterior X-ray view. In another embodiment, the human is directed to hold the object substantially above the head to move the scapula, preferably so that, once again, the scapula is relocated for an anterior-posterior X-ray view. The human may be a young child.

According to another aspect of the invention, there is provided a method of taking x-rays of a human, the method comprising: placing a shaped object in the hands of the human receiving the x-ray; and directing the human to hold the shaped object in a specified manner such that the position of the human when holding the object in the specified manner causes internal body components of the human to be located relative to each other in a preferred manner for the x-ray.

In accordance with one aspect of the invention, there is provided an object for holding by a person during an x-ray, the object being configured and/or shaped so as to assist the patient in moving body parts, and particularly the arms, into a position to allow for the taking of a better x-ray.

In accordance with another aspect of the invention, there is provided a method of positioning the body parts of a patient, typically the arms, in such a position whereby an optimal, clearer or enhanced x-ray image may be obtained.

One important preferred application of the present invention relates to the x-raying of certain internal organs which may be located in the thorax or the abdomen. The thorax comprises the chest, ribs, heart, lungs and clavicle. The scapula is in the rear of the chest. These organs to be X-rayed may include, for example, the lungs and heart, although other organs are not of course excluded. Furthermore, the invention is particularly useful for the taking of x-rays of young children, in order to assist and help such children in moving their arms to a desired position so that a good x-ray image can be obtained. Young children may be distracted or nervous, and the present invention facilitates not only the better positioning of the child for the x-ray, but may also help the child relax by diverting his attention and/or providing amusement.

In one preferred embodiment, the method and apparatus of the invention facilitates the removal or repositioning of the patient's scapulas when an x-ray of the lung field is taken. Particularly, the scapula position can be moved or relocated when the x-ray view is an anterior-posterior view, or a front view, and may also be useful in obtaining a lateral view x-ray of such organs.

In order to properly move the scapula to a position so that it interferes as little as possible with the x-ray image, the arms of the patient are typically raised above the head. While some movement of the scapula occurs when raising the arms upwardly to the horizontal, and even beyond, this often results in insufficient movement of the scapulae to reposition so as to them in a non-interfering manner for the purposes of securing the x-ray.

In one form of the invention, there is preferably provided an object, preferably but certainly not necessarily, in the shape of a large or oversized ball, which may be substantially lightweight, and which is preferably comprised of a material that does not interfere with the x-ray. The object, such as the ball, may be configured and shaped so that the natural tendency in holding the ball above the head, based on the dimensions and characteristics of the ball, is such that the scapula will tend to be moved upwardly and/or outwardly to a maximum extent, thereby substantially removing it from the x-ray field. The object may also be configured so that it can be comfortably and naturally held against the chest with the chin resting on the object.

While the preferred shape of the object is that of a ball, any suitably shaped object may be used. Such shapes could include rectangles, square blocks or indeed, any irregular shaped object or combination of shapes which may best be suited to the patient, taking into account size, age and such other parameters as may be relevant. Two or more such objects may also be releasably connectable to each other so that the size of the object can be selectively adjusted for optimal application.

In one form of the invention, the object may include handles, or other mechanisms to facilitate the holding or grasping of the object, preferably at or in a position thereof which tends to move the patient's arms into a position for optimal scapula placement during the x-ray procedure. The handles may be adjustable so that they are optimally dimensioned for the particular user.

In accordance with another aspect of the invention, there is provided a method for optimal scapula placement during x-rays, the method comprising providing the patient with a suitably configured and dimensioned object, such as a ball, for holding above the head, on or against the chest, or in some other appropriate and useful location, in such a manner so as to position the scapula as optimally as feasible during the x-ray procedure.

Preferably, the object is comprised of a high density foam. This makes it lightweight and easy to hold, especially by young children who may not have sufficient strength to hold heavy objects. Also, preferably, the object is comprised of a radio-lucent material and/or composition, so as not to interfere with the electromagnetic waves of the x-ray. In this way, the object can be held by the user in any position, even between the x-ray machine and the patient, which will best suit the x-ray required without interfering with the x-ray process.

In one preferred form, the object comprises a ball, preferably about beach-ball size, and, in yet another preferred embodiment, may comprise a ball of diameter of, for example, 31 inches, 45 inches or any range in between.

The ball may preferably be comprised of a polyurethane foam. Such polyurethane foam may be open-fill, high density, or a combination thereof.

Preferably, the ball further comprises a cover member for mounting on the object and the cover member may be disposable and comprises a radiolucent material. In one form of the invention, the cover member comprises a sealable opening through which the object can pass when the cover member is mounted on or removed from the object.

The invention is of particular use for x-raying children, especially children aged between one and six years of age. Most children will not resist holding a ball overhead, so that the apparatus and method of the invention not only allows optimal placement of the scapula, but also improves the comfort level of, and provide a distraction for, young patients so that an otherwise daunting x-ray procedure may, at least to some extent, become a game.

The method and object of the invention thus ensures that the arms are open, both raised upwardly and away from the thorax, so that the scapula is removed from the lung field, so that x-rays of this field, with the patient's arms raised, provide better medical information.

The device may be used by a patient, whether standing, or lying down on a bed or some other surface, during the course of the taking of a x-ray image.

DETAILED DESCRIPTION OF THE INVENTION

The invention is for a method and an apparatus which results in a patient undergoing an x-ray being positioned so as to help obtain an optimal or improved x-ray image. One preferred form of the invention relates to its use in moving the scapulae of the patient during an x-ray of the lung field, the scapula being moved, to the extent possible, to a position which exposes the lung field for an optimal x-ray.

Figure 1:
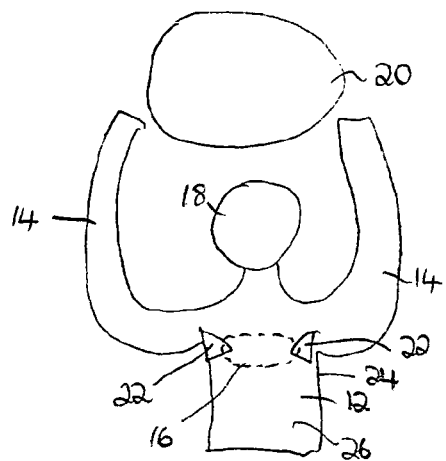
FIG. 1 is a schematic diagram of a person holding an object in accordance with the present invention, showing the position of the scapula preferred from the x-ray.
Figure 2:
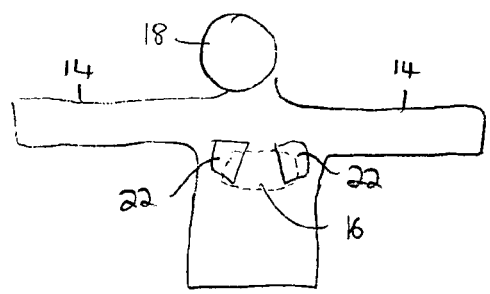
FIG. 2 is a schematic representation showing a patient with outstretched arms, indicating the approximate position of the scapula, which are not optimally placed for the x-ray.

With reference to the drawings, FIG. 1 shows in schematic form a patient 12 whose arms 14 are positioned optimally for an x-ray of the lung field, indicated generally by reference numeral 16. It will be noted that, above the patient's head 18, an object in the shape of a ball 20 is held. When holding the ball 20 above the head 18, the arms are moved up and away from the body 26 of the patient 12. In so doing, the locations of the scapulae 22 are moved in the upper torso, so that they are positioned towards the side 24 of the body 26, and upwardly as well. In such a position, the lung field 16 has less or minimal overlap with respect to the scapulae 22, so that a better x-ray image of the lung field 16 can be achieved. This is in contrast to the situation shown in FIG. 2 of the drawings, where the arms 14 are only shown in a laterally outstretched position. In this FIG. 2, it will be seen that the scapulae 22 do not move to the extent that they are able, and that they overlap, cover, or shield the lung field 16 in a manner which causes some avoidable interference with the resulting x-ray image, thereby compromising the amount of information that can be secured from the x-ray and making it less valuable as a medical diagnostic procedure.

The invention can, of course, be used with people of all ages. However, it is particularly helpful when taking x-rays of young children. Adults, or even older children are able to respond to directions from an x-ray technician to place the arms in a desired position, and hold them in that position for an extended period, while the x-ray image is formed. However, young children not only have difficulty keeping the position, but also may be afraid or uncooperative. Further, they may be easily distracted by other surroundings. With young children, therefore, the method and apparatus of the invention has a very useful application to encourage and assist the young child to reach and hold a preferred position or body posture. Therefore, the taking of the x-ray can be made into something entertaining and resembling a game, not only improving the potential medical results, but also making the child more comfortable and cooperative.

Figure 3:
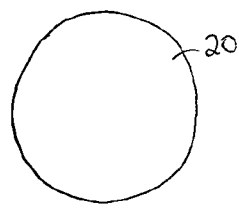
FIG. 3 is a perspective view of a ball, comprising the object used in the present invention for positioning the patient.

FIG. 3 shows one embodiment of the invention, which is simply a ball 20, preferably but not necessarily of approximately beach ball size. The ball 20 is preferably comprised of a polyurethane foam, which may be of the open-fill polyurethane, or a high density polyurethane, type or a combination thereof. However, any material which is preferably lightweight may be used, and, additionally, the ball 20 should comprise at least in part a radio-lucent material so as not to interfere with the x-ray result.

Figure 4:
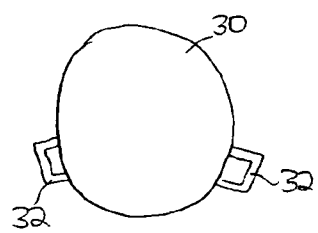
FIG. 4 is a perspective front view of another embodiment in accordance with the present invention.

FIG. 4 shows yet a further embodiment, comprising a ball 30 which has lateral handles 32. Such handles may be useful for young children to more easily grasp the ball and hold it in position. The handles 32 may also be positioned to encourage the patient to hold the ball in a particular manner and thereby position the arms correctly for the x-ray. While the handles 32 shown in FIG. 4 of the drawings are of a particular shape, it is not intended that this invention be limited to an object with handles 32 of the shape illustrated in this figure. Any type of grasping mechanism to improve the connection with the ball 30 may be used.

The ball 30 is, as mentioned, approximately beach ball size. One preferred size is 31 inches, and another preferred size is 45 inches in diameter. However, this is not intended to be a limiting factor, and any size range of balls may be provided. In addition, the patient may be requested to hold a ball 30 in each hand raised above the head, and these balls or other shaped objects may be connected, such as by a string, or another type of connecting piece.

Figure 5:
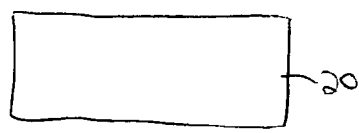
FIG. 5 is a front view of yet a further embodiment in accordance with the present invention.
Figure 6:
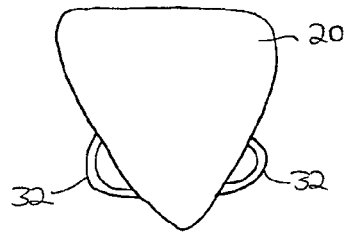
FIG. 6 is a front perspective view of still a further embodiment of an object in accordance with the present invention.

FIG. 5 of the drawings shows a further embodiment of the invention, namely, an object 20 which is of approximate rectangular shape. This object 20 may have handles or other mechanisms for holding it located at suitable parts thereof. FIG. 6 of the drawings shows yet a further embodiment of the invention, where the object 20 is more or less triangular in shape, with handles 32 located on each side and towards the lower end thereof. The position of the handles 32 shown in FIG. 6 is exemplary only and may be elsewhere on the object. The handles in this and other embodiments may even conveniently be movable or adjustable so that these handles may be selectively situated on the surface of the object based on the size and shape of the particular patient.

Figure 7:
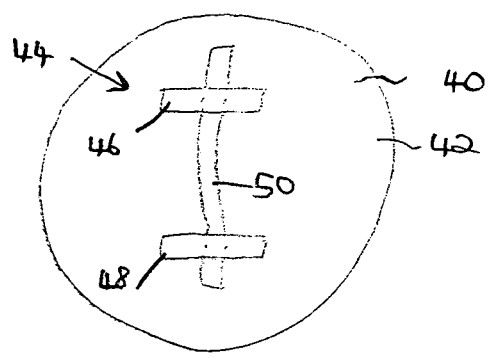
FIG. 7 is a side view of a ball of another embodiment in accordance with the present invention.

FIG. 7 of the drawings shows a side view of a ball 40 in accordance with the invention with a modified form of handle 44 on the outer surface 42 of the ball 40. The handle 44 comprises a pair of connector pieces 46 and 48 which stitch or sew down a holder 50 to the outer surface 42. The user slides his/her hands or even arms under the holder 50 to effectively hold the ball 40 during the x-ray.

Figure 8:
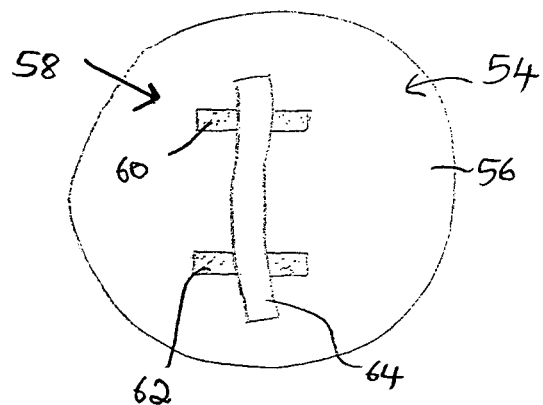
FIG. 8 is a side view of a ball of yet another embodiment in accordance with the present invention.

FIG. 8 of the drawings shows a side view of a ball 54 in accordance with another aspect of the invention having a handle 58 located on the outer surface 56 of the ball 54. This handle 58 can be adjusted to suit the particular user. The handle 58 comprises a pair of connector strips 60 and 62 which are stitched, glued, sewn or otherwise attached to the outer surface 56 of the ball 54. The upper or exposed surface of each of the connector strips 60 and 62 has a Velcro™ configuration. A holder strap 64 releasably connects to the connector strips 60 and 62. The holder strap 64 is longer than the distance between the connector strips 60 and 62 and has at least surface thereof, or a part of that surface, in a Velcro™ configuration. In use, the holder strap 64 can be pulled off the connector strips 60 and 62 and reapplied thereto so as to provide a comfortable slot or space between the outer surface 56 of the ball 54 and the holder strap 64. The space can be smaller for smaller users or where a firmer hold of the ball is required, or it may be larger for bigger users or where a more relaxed hold on the ball 54 is acceptable.

Figure 9:
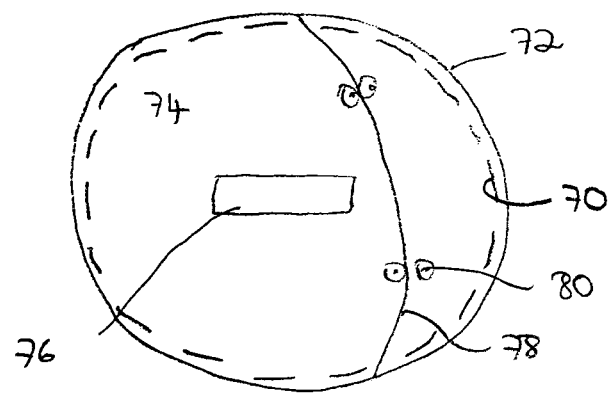
FIG. 9 is a view of a further embodiment in accordance with the present invention which shows the use of a cover on the ball.

Reference is now made to FIG. 9 of the drawings. FIG. 9 of the drawings illustrates schematically one embodiment of an object or ball 70 in accordance with the present invention, which can be of any one or more of the types described above with respect to the previous figures or description. The ball 70 is covered or blanketed with a cover 72 which preferably is much the same shape as the ball 70 itself, and establishes a fairly close fit on the ball 70 so movement of the cover when mounted on the ball is prevented or significantly reduced. The cover 72 has an outer surface 74 which may have a handle 76 of any suitable configuration for grasping by the user to secure a better grip of the ball 70.

The cover 72 also has a closable opening 78 which allows the ball 70 to be removed from the cover 72. By opening or closing the opening 78, the cover 72 may be removed and replaced as needed. Typically, the cover 72 would preferably be replaced after each use. Since the ball of the invention is used in a medical setting and cleanliness and high standards of sanitation are imperative to avoid spread of germs and diseases, the cover 72 will customarily be used once only for a particular set of X-rays on a patient and then removed and discarded. A fresh, unused cover 72 would then be placed on the ball 70 for the next user to ensure that any of the patient's bodily fluids such as tears, saliva, sweat, vomit and/or blood are not transmitted to the next user.

The opening 78 may take any number of suitable forms. It may be slit closable by tabs or buttons 80 as shown in FIG. 9, or it may be closable by a zipper of some kind, Velcro™ and the like. The opening 78 may be a slit as shown in the drawing, or it may comprise a flap which can be opened. Further, the opening 78 may be in the form of a resealable door.

Preferably, the covers 72 are kept in an hermetic, sealed environment before use, and disposed of after use in accordance with conventional medical procedures for getting rid of potentially harmful products. The cover 72 of course prevents the bodily fluids of the patient or other workers from touching or being absorbed by the often porous nature of the ball 70. The material from which the cover 72 is made will of course be chosen so that it does not interfere with the X-ray process, and will be wholly or partially radiolucent.

A single object or ball of the invention may have a plurality of handles or holders thereon, and the handles or holders on a particular ball may be the same as each other or they be different to best suit the needs of the users and the requirements of the x-ray technologist.

It should be noted that the various shapes illustrated are intended to be exemplary only, and the invention is not in any way limited to an object of such shape. Any shaped object, whether of a specific type, a combination of shapes, or indeed, some irregular shape, may be used, as long as it achieves the purposes of the present invention.

The invention is not limited to the precise details described herein.

The invention claimed is:

1. A holder for use in x-rays, the holder comprising a shaped object to be held by a person while undergoing an x-ray, the shaped object having an outer surface defining an enclosed space and filler matter in the enclosed space, the outer surface and filler matter being comprised of a high density, radiolucent polyurethane material, the holder having a pair of handles for holding and which are releasably secured to the outer surface of the holder so that the position of the handles can be varied on the outer surface based on the size of the person undergoing the x-ray.

2. A holder as claimed in claim 1 wherein the shaped object has a shape selected from: spherical, round, square, rectangular, triangular, polygonal, geodesic.

3. A holder as claimed in claim 1 wherein the pair of handles are on substantially opposing sides of the ball shaped object, the handles comprising outwardly extending grip members having ends which are secured to the outer surface of the ball shaped object.

4. A holder as claimed in claim 1 wherein the handle comprises a flat elongate strip having opposing ends, and fastening means for securing the flat elongate strip to the outer surface near the opposing ends thereof.

5. A holder as claimed in claim 1 wherein the handle is adjustable in size.

6. A holder as claimed in claim 5 wherein the adjustable handle comprises:
   a first band and a second band of fabric secured to the outer surface of the shaped object at a selected distance from each other, the first and second bands each having an outer surface at least a portion of which has a textured configuration; and
   a grip member extending at least between the first and second bands, the grip member having a surface at least a portion of which has a Velcro™ textured configuration so that the grip member can be releasably attached to and removed from first and second bands in various arrangements.

7. A holder as claimed in claim 1 wherein both the outer surface of the shaped object and the filler matter are both comprised entirely of radiolucent material.

8. A holder as claimed in claim 1 wherein the filler matter is comprised of a lightweight material.

9. A holder as claimed in claim 1 wherein the filler matter is comprised of high density foam.

10. A holder as claimed in claim 1 wherein the shaped object is a ball of diameter between 30 and 45 inches.

11. A holder as claimed in claim 1 wherein the filler matter is comprised of polyurethane foam.

12. A holder as claimed in claim 1 further comprising a cover member for mounting on the object.

13. A holder as claimed in claim 12 wherein the cover member is disposable and comprises a radiolucent material.

14. A holder as claimed in claim 12 wherein the cover member comprises a sealable opening through which the object can pass when the cover member is mounted on or removed from the object.

\* \* \* \* \*